US009980858B2

(12) United States Patent
Roe

(10) Patent No.: US 9,980,858 B2
(45) Date of Patent: May 29, 2018

(54) ABSORBENT ARTICLE WITH IMPROVED GARMENT-LIKE CHARACTER

(71) Applicant: The Procter & Gamble Company, Cincinnati, OH (US)

(72) Inventor: Donald Carroll Roe, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 605 days.

(21) Appl. No.: 13/757,031

(22) Filed: Feb. 1, 2013

(65) Prior Publication Data
US 2013/0144245 A1 Jun. 6, 2013

Related U.S. Application Data

(63) Continuation of application No. 11/528,412, filed on Sep. 27, 2006, now abandoned.

(51) Int. Cl.
A61F 13/15 (2006.01)
A61F 13/20 (2006.01)
A61F 13/56 (2006.01)
A61F 13/49 (2006.01)
A61F 13/58 (2006.01)
A61F 13/62 (2006.01)

(52) U.S. Cl.
CPC .... A61F 13/5633 (2013.01); A61F 13/15203 (2013.01); A61F 13/49015 (2013.01); A61F 13/58 (2013.01); A61F 13/622 (2013.01)

(58) Field of Classification Search
USPC ........................................ 604/386–390, 396
See application file for complete search history.

(56) References Cited

U.S. PATENT DOCUMENTS

| 3,848,594 A | 11/1974 | Buell |
| 3,860,003 A | 1/1975 | Buell |
| 4,610,678 A | 9/1986 | Weisman et al. |
| 4,662,875 A | 5/1987 | Hirotsu et al. |
| 4,673,402 A | 6/1987 | Weisman et al. |
| 4,699,622 A | 10/1987 | Toussant et al. |
| 4,808,178 A | 2/1989 | Aziz et al. |
| 4,662,875 B1 | 4/1989 | Hirotsu et al. |
| 4,834,735 A | 5/1989 | Alemany et al. |
| 4,846,815 A | 7/1989 | Scripps |
| 4,888,231 A | 12/1989 | Angstadt |
| 4,892,536 A | 1/1990 | Desmarais et al. |
| 4,894,060 A | 1/1990 | Nestegard |

(Continued)

Primary Examiner — Michele M Kidwell
(74) Attorney, Agent, or Firm — William E. Gallagher

(57) ABSTRACT

A disposable absorbent article may include a chassis comprising a liquid permeable topsheet, a backsheet, and an absorbent core disposed between the topsheet and backsheet; and an ear joined to the rear waist region of the chassis such that at least a portion of said ear extends laterally outward from the longitudinal edge of the chassis in the rear waist region. The article further comprises a fastening system including an engaging member disposed proximate to distal edge of the ear and a receiving member disposed on the chassis in the front waist region, wherein the ear interconnects the front waist region and the rear waist region upon engagement of the engaging member with the receiving member. The ear has a Front Edge Displacement and a Rear Edge Displacement such that a sum of the Front Edge Displacement and the Rear Edge Displacement is no greater than about 12 mm.

12 Claims, 9 Drawing Sheets

(56) References Cited

U.S. PATENT DOCUMENTS

| | | |
|---|---|---|
| 4,909,803 A | 3/1990 | Aziz et al. |
| 4,946,527 A | 8/1990 | Battrell |
| 4,963,140 A | 10/1990 | Robertson et al. |
| 4,990,147 A | 2/1991 | Freeland |
| 5,037,416 A | 8/1991 | Allen et al. |
| 5,137,537 A | 8/1992 | Herron et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,221,274 A | 6/1993 | Buell et al. |
| 5,242,436 A | 9/1993 | Weil et al. |
| 5,260,345 A | 11/1993 | Desmarais et al. |
| 5,269,775 A | 12/1993 | Freeland et al. |
| 5,342,338 A | 8/1994 | Roe |
| 5,387,207 A | 2/1995 | Dyer et al. |
| 5,397,316 A | 3/1995 | Lavon et al. |
| 5,454,803 A | 10/1995 | Sageser et al. |
| 5,499,978 A | 3/1996 | Buell et al. |
| 5,507,736 A | 4/1996 | Clear et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,591,152 A | 1/1997 | Buell et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,588 A | 7/1997 | Roe et al. |
| 5,685,874 A | 11/1997 | Buell et al. |
| 5,846,262 A | 12/1998 | Sayama et al. |
| 5,865,823 A | 2/1999 | Curro |
| 5,931,827 A | 8/1999 | Buell et al. |
| 6,004,306 A | 12/1999 | Robles et al. |
| 6,030,373 A | 2/2000 | VanGompel et al. |
| 6,107,537 A | 8/2000 | Elder et al. |
| 6,120,487 A | 9/2000 | Ashton |
| 6,182,412 B1 | 2/2001 | Traxler |
| 6,432,098 B1 | 8/2002 | Kline et al. |
| 6,453,628 B2 | 9/2002 | Traxler |
| 7,014,324 B2 | 3/2006 | Hang |
| 7,626,073 B2 | 12/2009 | Catalan |
| 8,246,598 B2 | 8/2012 | Vogt et al. |
| 2002/0032427 A1 | 3/2002 | Schmitz et al. |
| 2007/0073260 A1 | 3/2007 | Roe |

ABSORBENT ARTICLE WITH IMPROVED GARMENT-LIKE CHARACTER

FIELD OF INVENTION

This invention relates to absorbent articles such as diapers having fastener bearing ears that yield a more garment-like article. The absorbent article may have improved functional characteristics and communicative properties.

BACKGROUND OF THE INVENTION

It has long been known that absorbent articles such as conventional taped diapers offer the benefit of receiving and containing urine and/or other bodily exudates. To effectively contain exudates, the article should provide a snug fit around the waist and legs of a wearer. Absorbent articles are known to have a chassis comprising a topsheet, a backsheet, and an absorbent core. Absorbent articles such as conventional taped diapers generally include a front and a rear waist section releasably and/or refastenably connected by a fastening system. The fastening system generally comprises an engaging member and a receiving member. The engaging member may be an adhesive tape, a hook bearing tape, a cohesive tape, or other like structure. The receiving member may be an element or zone on the article that may receive the engaging member such as a polymer film landing zone (viz., for receipt of the adhesive or cohesive tape) or a loop bearing surface (viz., for receipt of the hook bearing tape). The engaging member may be joined to the receiving member thereby interconnecting the rear waist section to the front waist section and thereby forming a waist opening and a pair of leg openings.

Current diaper designs frequently include the use of extensible ears. Back ears may extend laterally from the longitudinal edge of the rear waist section of the chassis. The engaging member of the fastening system may be attached to the back ear. In the case of front-fastened or taped designs, when the fastening system is engaged to the receiving member on the front waist region, the back ear serves as an interconnecting member between the front waist section and the rear waist section, which together form a waist opening and pair of leg openings. Back ears may be constructed to provide a degree of elastic recovery. Elasticized back ears allow the diaper to provide a more customized fit. Furthermore, the elastic capability allows the diaper to adjust to the forces exerted by the wearer without causing permanent deformation of the diaper or discomfort for the wearer of the diaper. Elasticity is typically imparted to the back ears by incorporating elastic materials into the ear. Due to the high cost of elastomeric materials, a common practice is to construct elastic ears as discrete components that are attached to the chassis (i.e., the main absorbent assembly to which other components may be disposed) resulting in a multipiece diaper. While this practice results in the efficient and cost-effective use of elastic materials, it is not without problems.

One problem seen in multipiece diapers is "tophatting." A "tophat" is a portion of the front or rear waist region that extends beyond, the uppermost edge of the front or back ear toward the waist edge of the diaper. When a multipiece diaper is appropriately worn, the waist edge of the diaper in the front waist region and the rear waist region are substantially linear or slightly curvilinear. As the waist edge transitions from the rear waist region to the attached back ear, the waist edge may abruptly drop and then continue in a linear or curvilinear manner following the upper edge of the back ear. This "drop" from the waist edge in the front waist region or the rear waist region to the upper edge of the back ear may be one centimeter or greater. When worn, a taped diaper with the drop in the waist edge appears to have a notch cut from its side. The waist edge of such a diaper may have a stair step-like appearance.

Tophatting may have an adverse impact on the fit characteristics of a multipiece diaper. Generally, a diaper exerts a circumferential line of tension around a wearer's torso. This tension may be a product of the elastic back ear being strained. With a multipiece diaper exhibiting a tophat, the line of tension is located well below the waist edge because the line of tension is transmitted only along or through a continuous, unbroken path about the diaper. Since the tension-generating elasticized ear and fastening system are significantly remote from the waist edge, the line of tension is likewise remote from (e.g., generally lower than) the waist edge in the front waist region and rear waist region.

Fit and functionality problems may result from the line of tension being located remotely from the waist edge. For example, the front waist region and/or rear waist region of the diaper may exhibit sagging or fold-over. Sagging is the wrinkled, loose, gapped, or puckered configuration that the diaper exhibits when it is not under tension. Fold-over is the inversion of at least a portion of the diaper such that a body-facing surface of the diaper becomes garment-facing. Similar to sagging, fold-over may occur when the portion of the diaper is not under tension. Fold-over and sagging may also impair the gasketing function of the waist edge. For example, the interface of the waist edge and the wearer's waist is susceptible to leakage particularly when the wearer is in a prone or supine position. Fold-over and sagging can reduce the surface area of the diaper that is hi close contact with the wearer at this interface which may result in leakage.

Furthermore, fold-over and sagging are aesthetically undesirable. Fold-over and sagging result in a diaper that is sloppy looking during wear. This, in turn, may communicate to the consumer that the diaper is of low quality which may be contrary to the high quality of functional characteristics such as absorbency or leakage prevention.

Top-hatting and the resulting lack of a smooth, continuous, and circumferential waist edge communicate other unwanted messages to the consumer or wearer of the diaper. For example, tophatting may be a readily visible signal that the product is a diaper. For many wearers such as children being toilet trained or incontinent youths and adults, a stigma is attached to having to wear a diaper. To alleviate this concern, the diaper should communicate a message of being garment-like or underwear-like. In other words, it is desirable that the diaper not appear diaper-like. However, tophatting and discontinuous waist edges are apparent signals of a diaper.

Accordingly, it would be desirable to provide a diaper having a back ear that eliminates or reduces tophatting in a multipiece diaper. Furthermore, it is desirable that the diaper exhibit a smooth, continuous, circumferential waist edge without discontinuities or drops. It is desirable that the diaper exhibit a line of tension, which is provided at least in part by discrete ears, as close to the waist edge as possible. It is also desirable that the diaper communicate a message of being garment-like without the readily apparent visual cue (e.g., waist discontinuity) of being a diaper.

SUMMARY OF THE INVENTION

The present invention relates to a disposable absorbent article comprising a chassis having a front waist region with a front waist edge, a rear waist region with a rear waist edge, a crotch region between the front waist region and the rear waist region, and a pair of opposing longitudinal edges. The chassis may comprise a topsheet, a backsheet, and an absorbent core disposed between the topsheet and backsheet. The chassis may further comprise an ear having an upper lateral edge, a proximal edge, and a distal edge, wherein the ear is joined to the rear waist region of the chassis such that at least a portion of said ear extends laterally outward from the longitudinal edge of the chassis in the rear waist region. The chassis may further comprise a fastening system comprising an engaging member disposed proximate to distal edge of the ear, and a receiving member disposed on the chassis in the front waist region, wherein the ear interconnects the front waist region and the rear waist region upon engagement of the engaging member with the receiving member. The ear may have a Front Edge Displacement and a Rear Edge Displacement such that a sum of the Front Edge Displacement and the Rear Edge Displacement is no greater than about 12 mm.

In certain embodiments of the present invention, the disposable absorbent article may comprise a front ear and a bade ear. The front ear may have a Front Edge Displacement and the back ear may have a Rear Edge Displacement such that a sum of the Front Edge Displacement and the Rear Edge Displacement is no greater than about 12 mm.

DETAILED DESCRIPTION OF THE INVENTION

Figure 1A:
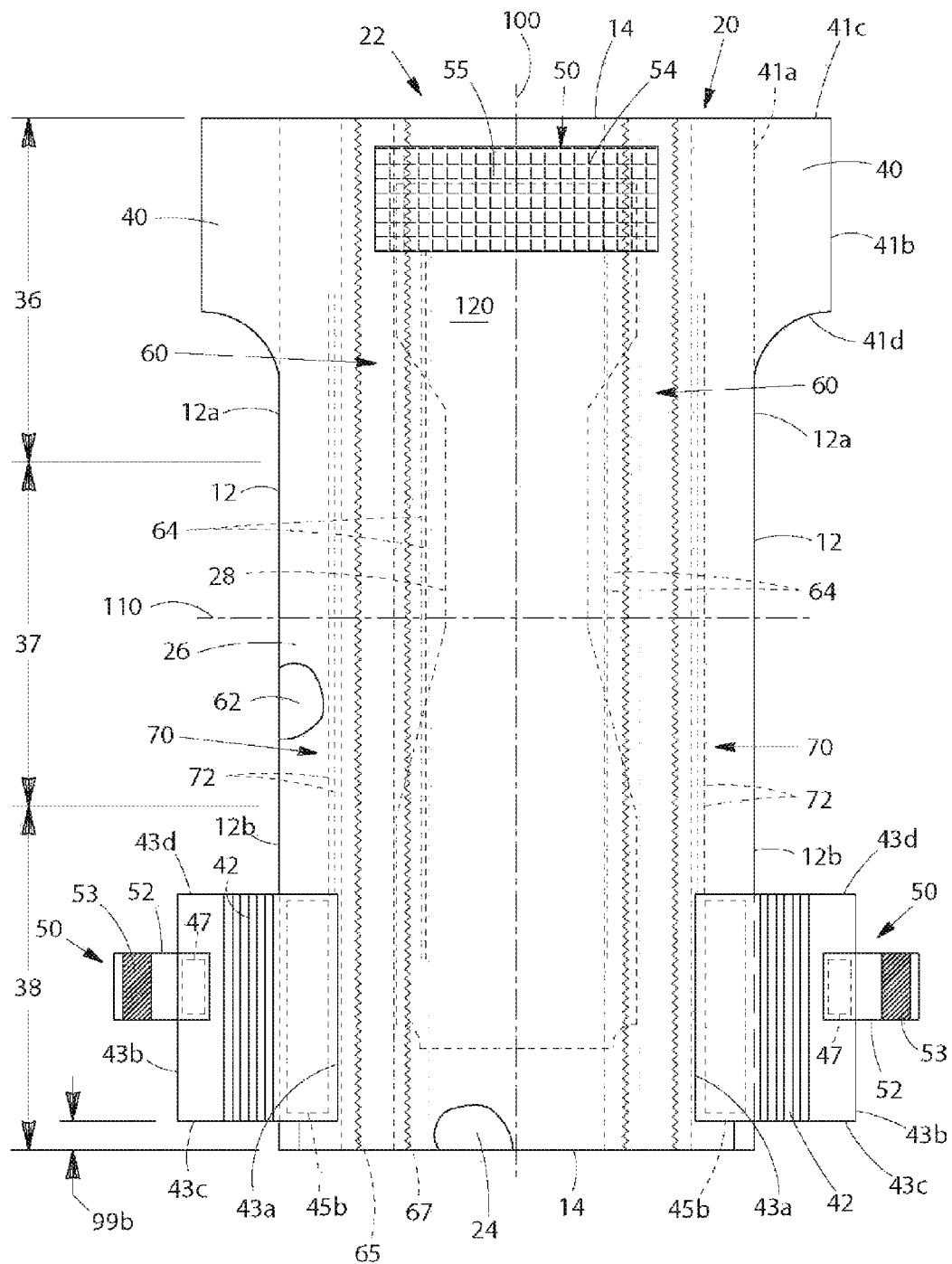
FIG. 1A is a plan view of an exemplary diaper in a flat, uncontracted state with back ears.

As used, herein, the following terms shall have the meaning specified thereafter:

"Tophat" is a portion of a front or rear waist region of a diaper that extends beyond the uppermost edge of a front or back ear toward the waist edge of the diaper.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void, spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable." As is well known in the art, a common method for measuring the permeability to water, urine, or synthetic urine of the materials typically used in absorbent articles is a hydrostatic pressure test, also called a hydrostatic head test or simply a "hydrohead" test. Suitable well known compendial methods for hydrohead testing are approved, by INDA (formerly the International Nonwovens and Disposables Association, now The Association of the Nonwoven Fabrics Industry) and EDANA (European Disposables And Nonwovens Association).

"Extendibility" and "extensible" mean that the width or length of the component in a relaxed, state can be extended or increased.

"Elasticated" and "elasticized" mean that a component comprises at least a portion made of elastic material.

"Elastic," "elastomer," and "elastomeric" refer to a material which generally is able to extend to a strain of at least 50% without breaking or rupturing, and is able to recover substantially to its original dimensions after the deforming force has been removed.

"Elastomeric material" is a material exhibiting elastic properties. Elastomeric materials may include elastomeric films, scrims, nonwovens, and other sheet-like structures.

"Outboard" and "inboard" refer respectively to the location of an element disposed relatively far from or near to the longitudinal centerline of the diaper with respect to a second element. For example, if element A is outboard of element B, then element A is farther from the longitudinal centerline than is element B.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Prefastened" refers to a disposable absorbent article that is manufactured such that the fastening system is in an engaged, or fastened configuration.

"Consumer Commercial Good" refers to an item produced and distributed, in large quantities and that the item may be purchased by a consumer through a retail establishment accessible to the public.

"Linear Projection" is the linear extension of an edge beyond the end point of the edge.

FIG. 1 is a plan view of an exemplary, non-limiting embodiment of a diaper 20 of the present invention in a flat, uncontracted state (i.e., without elastic induced contraction). The garment-facing surface 120 of the diaper 20 is facing the viewer. The diaper 20 includes a longitudinal centerline 100 and a lateral centerline 110. The diaper 20 may comprise a chassis 22. The diaper 20 and chassis 22 are shown to have a front waist region 36, a rear waist region 38 opposed to the front waist region 36, and a crotch region 37 located between the front waist region 36 and the rear waist region 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The outer periphery of chassis 22 is defined by longitudinal edges 12 and lateral edges 14. The longitudinal edges 12 may be subdivided, into a front longitudinal edge 12a, which is the portion of the longitudinal edge 12 in the front waist region 36, and a rear longitudinal edge 12b, which is the portion of the longitudinal edge 12 in the rear waist region 38. The chassis 22 may have opposing longitudinal edges 12 that are oriented, generally parallel to the longitudinal centerline 100. However, for better fit, longitudinal edges 12 may be curved or angled to produce, for example, an "hourglass" shape diaper when viewed in a plan view. The chassis 22 may have opposing lateral edges 14 that are oriented generally parallel to the lateral centerline 110.

The chassis 22 may comprises a liquid permeable topsheet 24, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the diaper 20 with other features may added to form the composite diaper structure. While the topsheet 24, the backsheet 26, and the absorbent core 28 may be assembled in a variety of well-known configurations, preferred diaper configurations are described generally in U.S. Pat. Nos. 3,860,003; 5,151,092; 5,221,274; 5,554,145; 5,569,234; 5,580,411; and 6,004,306.

The topsheet 24 is generally a portion of the diaper 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. A particularly topsheet 24 is available from BBA Fiberweb, Brentwood, Tenn. as supplier code 055SLPV09U.

Any portion of the topsheet 24 may be coated, with a lotion as is known in the art. Examples of suitable lotions include those described in U.S. Pat. Nos. 5,607,760; 5,609, 587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

The absorbent core 28 may comprise a wide variety of liquid-absorbent materials commonly used in disposable diapers and other absorbent articles. Examples of suitable absorbent materials include comminuted wood, pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

The backsheet 26 is generally positioned such that it may be at least a portion of the garment-facing surface 120 of the diaper 20. Backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially water-impermeable film. The outer cover and an inner layer may be joined, together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled, in the art that various other changes and modifications can be made without departing from the spirit and scope of the invention.

The diaper 20 may include barrier cuffs 60 and/or gasketing cuffs 70. Gasketing cuffs 70 may also be referred to as outer leg cuffs, leg bands, side flaps, leg cuffs, or elastic cuffs. Barrier cuffs 60 may also be referred to as second cuffs, inner leg cuffs or "stand-up" elasticized flaps.

The gasketing cuff 70 may be substantially inelastic or may be elastically extensible to dynamically fit at the wearer's leg. The gasketing cuff 70 may be formed by one or more elastic members 72 (such as elastic strands) operatively joined to the topsheet 24, backsheet 26, or any other suitable substrate used, in the formation of the diaper 20. Suitable gasketing cuff construction is further described in U.S. Pat. No. 3,860,003

The barrier cuff 60 may span the entire longitudinal length of the diaper 20. The barrier cuff 60 may be formed by a flap 62 and an elastic member 64 (such as elastic strands). The flap 62 may be a continuous extension of any of the existing materials or elements that form the diaper 20. In other embodiments, such as shown in FIG. 1, the barrier cuff 60 may be a discrete element. In such embodiments, the barrier cuff 60 comprising the flap 62 and the elastic member 64 may be formed then joined to the chassis 22 by a bond 65.

The flap 62 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. In certain embodiments, the flap 62 may comprise a nonwoven web such as spunbond webs, meltblown webs, carded webs, and combinations thereof (e.g., spunbond-meltblown composites and variants). Laminates of the aforementioned substrates may also be used to form the flap 62. A particularly suitable flap may comprise a nonwoven available from BBA Fiberweb, Brentwood, Tenn. as supplier code 30926. A particularly suitable elastic member is available from Invista, Wichita, Kans. as supplier code T262P. Further description of diapers having barrier cuffs and suitable construction of such barrier cuffs may be found in U.S. Pat. Nos. 4,808,178 and 4,909,803. The elastic member 64 may span the longitudinal length of the barrier cuff 60. In other embodiments, the elastic member 64 may span at least the longitudinal length of the barrier cuff 60 within the crotch region 37. It is desirable that the elastic member 64 exhibits sufficient elasticity such that the barrier cuff 60 remains in contact with the wearer during normal wear, thereby enhancing the barrier properties of the barrier cuff 60. The elastic member 64 may be connected to the flap 62 at opposing longitudinal ends. In certain embodiments, the flap 62 may be folded, over onto itself so as to encircle the elastic member 64. A bond 67 may be used to secure the folded section of the flap 62.

The barrier cuffs 60 and/or gasketing cuffs 70 may be treated, in full or in part, with a lotion, as described above with regard to topsheets, or may be fully or partially coated with a hydrophobic surface coating as detailed in U.S. application Ser. No. 11/055,743, which was filed Feb. 10, 2005.

The diaper 20 may include front ears 40 and/or back ears 42. The ears 40, 42 may be extensible, inextensible, elastic, or inelastic. The ears 40, 42 may be formed from nonwoven webs, woven webs, knitted fabrics, polymeric and elastomeric films, apertured films, sponges, foams, scrims, and combinations and laminates thereof. In certain embodiments the ears 40, 42 may be formed of a stretch laminate such as a nonwoven/elastomeric material laminate or a nonwoven/elastomeric material/nonwoven laminate. Stretch laminates may be formed by any method known in the art. For example, the ears 40, 42 may be formed as a zero strain stretch laminate, which includes at least a layer of non-woven material and an elastomeric element. The elastomeric element is attached to the layer of non-woven material while in a relaxed, or substantially relaxed state, and the resulting laminate is made stretchable (or more stretchable over a further range) by subjecting the laminate to an activation process which elongates the nonwoven layer permanently, but the elastomeric element temporarily. The nonwoven layer may be integral with at least a portion of the chassis 22, in which case the elastomeric element may be attached to the nonwoven layer and the non-woven/elastomeric element laminate is subsequently activated. Alternatively, the nonwoven layer may be a separate component, in which case the elastomeric element is attached to the nonwoven layer to form the laminate, which is then coupled to the main portion. If one or more layers of the side panel are provided separately, the laminate may be activated either before or after attachment to the main portion. The zero strain activation processes is further disclosed in U.S. Pat. Nos. 5,167,897 and 5,156,793. A suitable elastic ear may be an activated laminate comprising an elastomeric film (such as is available from Tredegar Corp, Richmond, Va., as supplier code X25007) disposed, between two nonwoven layers (such as is available from BBA Fiberweb, Brentwood, Tenn. as supplier code FPN332).

The ears 40, 42 may be discrete or integral A discrete ear is formed as separate element which is joined to the chassis 22. An integral ear is a portion of the chassis 22 that projects laterally outward from the longitudinal edge 12. The integral ear may be formed by cutting the chassis form to have the projection.

Figure 1B:
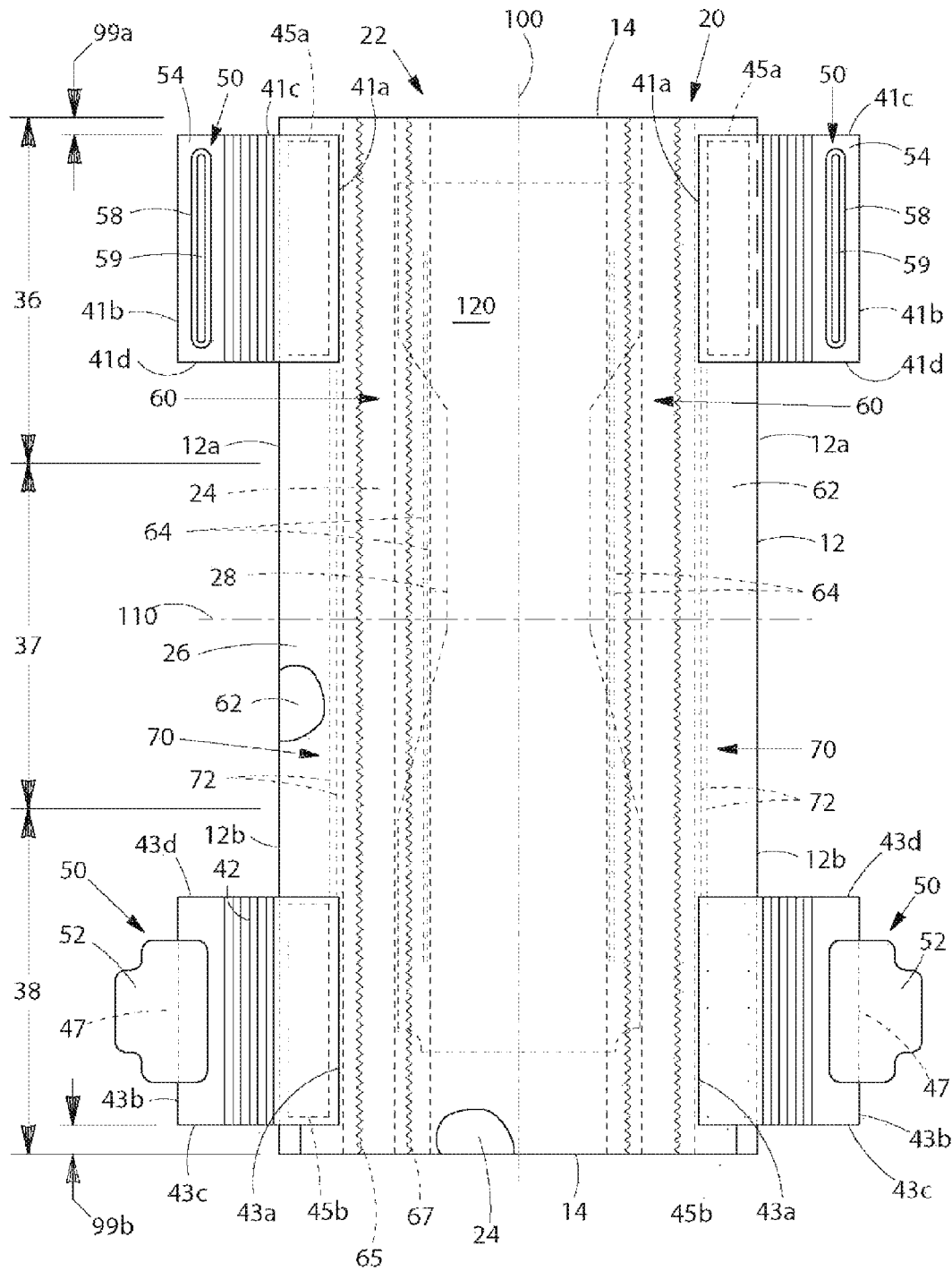
FIG. 1B is a plan view of an exemplary diaper in a flat, uncontracted state with front ears and back ears.

A suitable diaper 20 having discrete back ears 42 and integral front ears 40 is shown in FIG. 1A. A suitable diaper having discrete back ears 42 and discrete front ears 40 is shown in FIG. 1B. The front ears 40 may have a proximal edge 41a, a distal edge 41b, an upper edge 41c, and a lower edge 41d. A portion of the front ear 40 adjacent to the proximal edge 41a may be joined to the chassis 22 at a front bond region 45a. The front bond region 45a is the area within which one or more bonds join the discrete front ear 40 to the chassis 22. The front bond region 45a may comprise one or more bonds formed by any bonding method known in the art such as adhesive bonding, pressure bonding, heat bonding, and the like. If the front bond region 45a comprises more than one bond, such as in an array or pattern of bonds, the front bond region 45a is defined, by the are bounded, by a polygon connecting the outermost bonds in each dimension. There may be a degree of overlap between the front ear 40 and the chassis 12 to allow for bonding. However, in other embodiments, a larger portion of the front ear 40 may comprise a layer, element, or substrate of the chassis 22.

Figure 1C:
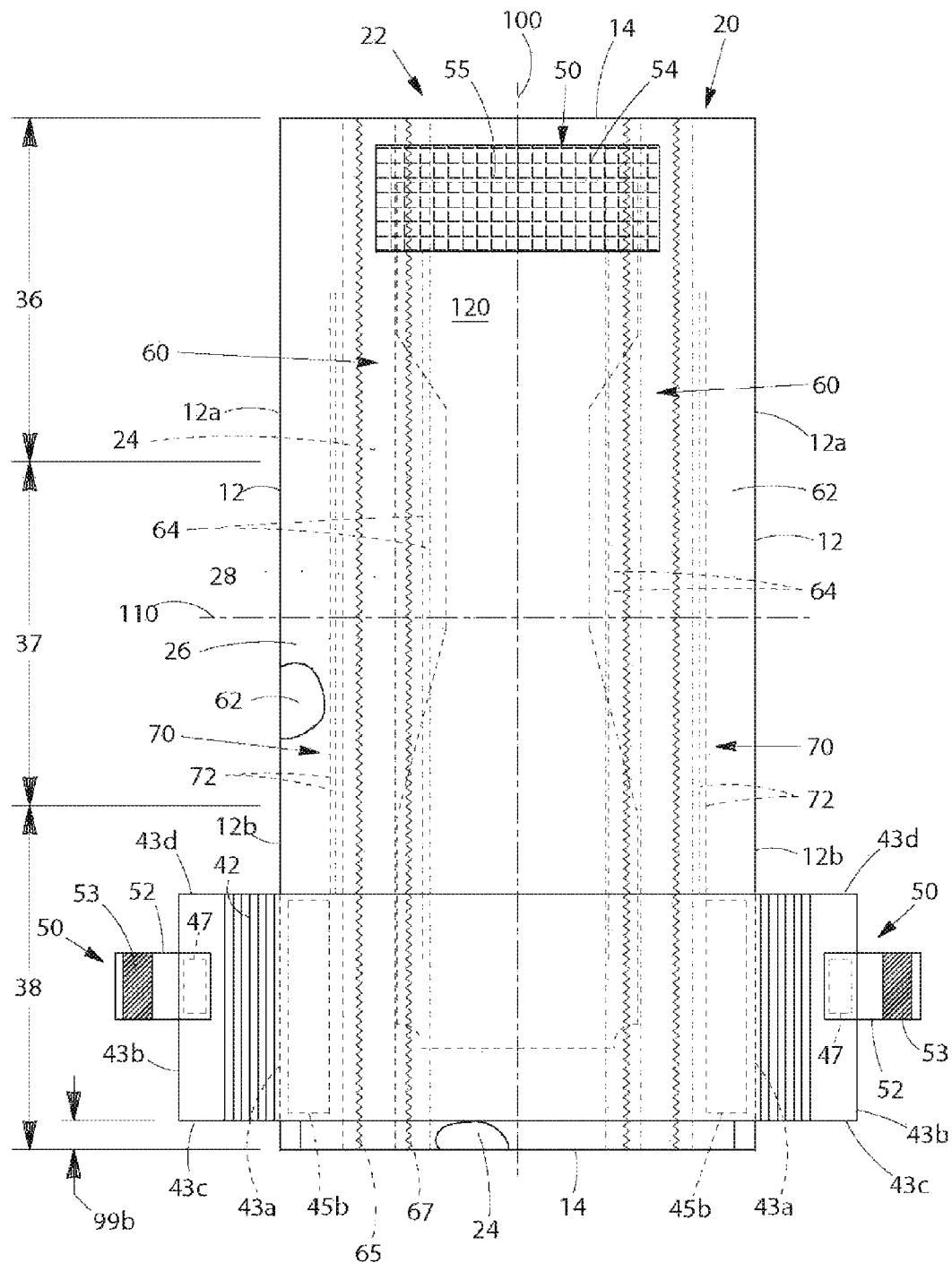
FIG. 1C is a plan view of an exemplary diaper in a flat, uncontracted state with back ears formed by a belt.

FIG. 1C depicts an embodiment of a diaper 20 having a belt 49 that forms both back ears 42. In this embodiment, no front ears are present. The belt 49 may extend beyond the opposing longitudinal edges 12. The back ears 42 may have a proximal edge 43a, a distal edge 43b, an upper edge 43c, and a lower edge 43d. The proximal edge 43a is taken as projection of the longitudinal edge 12 on the belt 49.

As shown in both FIGS. 1A-C, the back ear 42 may be a discrete element or a portion of a discrete element (e.g., the belt 45) that is joined to the chassis 22. The back ears 42 may have a proximal edge 43a, a distal edge 43b, an upper edge 43c, and a lower edge 43d. A portion of the back ear 42 adjacent to the proximal edge 43a may be joined to the chassis 22 at a back bond region 45b. The back bond region 45b is the area within which one or more bonds join the back ear 42 to the chassis 22. The back bond region 45b may comprise one or more bonds formed by any bonding method known in the art such as adhesive bonding, pressure bonding, heat bonding, and the like. If the back bond region 45b comprises more than one bond, such as in an array or pattern of bonds, the back bond region 45b is defined by the are bounded by a polygon connecting the outermost bonds in each dimension. There may be a degree of overlap between the back ear 42 and the chassis 12 to allow for bonding. However, in other embodiments, a larger portion or all of the back ear 42 may comprise a layer, element, or substrate of the chassis 22.

The diaper 20 may also include a fastening system 50. When fastened, the fastening system 50 interconnects the front waist region 36 and the rear waist region 38 resulting in a waist circumference that may encircle the wearer during wear of the diaper 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662, 875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963, 140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

FIG. 1A depicts a fastening system 50 having an engaging member 52 proximate the distal edge 43b of the back ear 42 and a receiving member 54 disposed in the front waist region 36 of the chassis 22. The engaging member 52 is shown having an engaging surface 53 that may comprise hooks, loops, an adhesive, a cohesive, or other fastening member. FIG. 1A depicts the engaging surface 53 as covering only a portion of the engaging member 52; however, in other embodiments, the engaging surface 53 may cover substantially all of one or more faces of the engaging member 52. The engaging member 52 may be joined to the back ear 42 at a fastener bond, region 47. The fastener bond region 47 is the area within which one or more bonds join the engaging member 52 to the back ear 42. The fastener bond region 47 may comprise one or more bonds formed by any bonding method known in the art such as adhesive bonding, pressure bonding, heat bonding, and the like. If the fastener bond region 47 comprises more than one bond, such as in an array or pattern of bonds, the fastener bond region 47 is defined by the are bounded by a polygon connecting the outermost bonds in each dimension. In certain cases, such as shown in FIG. 1B, the fastener bonding region 47 may be a line of attachment.

The receiving member 54 may have a receiving surface 55 (as shown in FIGS. 1A and 1C) that allows for engagement of the engaging member 52. The receiving surface 54 may comprise hooks, loops, an adhesive, a cohesive, or other fastening component that can receive the engaging member 52. Suitable engaging member 52 and receiving member 54 combinations include but are not limited to hooks/loop, hooks/hooks, adhesive/polymeric film; cohesive/cohesive, adhesive/adhesive; tab/slot; and button/button hole.

Figure 2A:
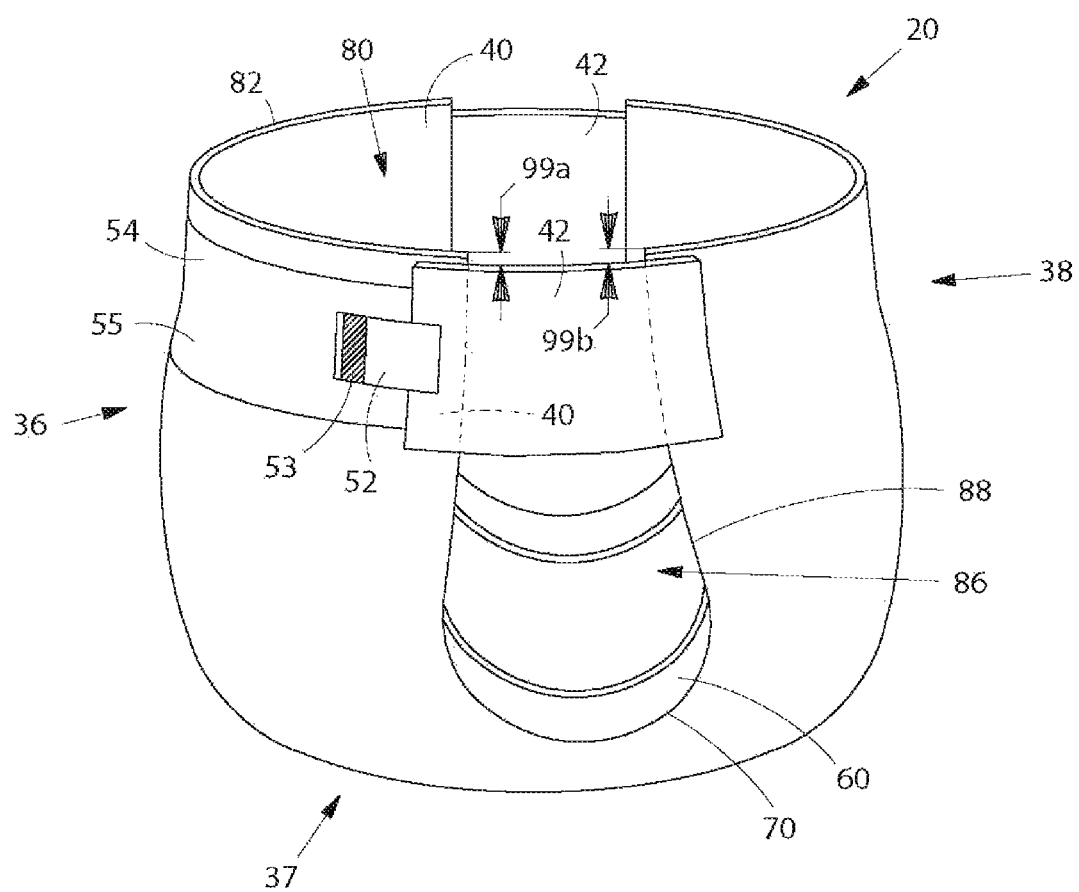
FIG. 2A is a perspective view of the diaper of FIG. 1A in a fastened configuration as would be exhibited during wear.

FIG. 2A is a perspective view of the diaper 20 of FIG. 1A in a fastened configuration as would be seen during normal wear of the diaper. The engaging surface 53 of the engaging member 52 may be mated with the receiving member 54. The back ear 42 may span and connect the front waist region 36 and the rear waist region 38 to form a leg opening 86 defined, by a leg edge 88 (which includes a portion of the longitudinal edge 12 and the lower edge 44d of the back ear 42) and a waist opening 80 defined by a waist edge 82 (which includes a portion of the lateral edges 14 of the chassis 22 and the upper edge 44c of the back ear 42). In embodiments where the back ear 42 is extensible or elastic, the back ear 42 may be extended to provide a tensioning force to the diaper 20 during wear.

Figure 2B:
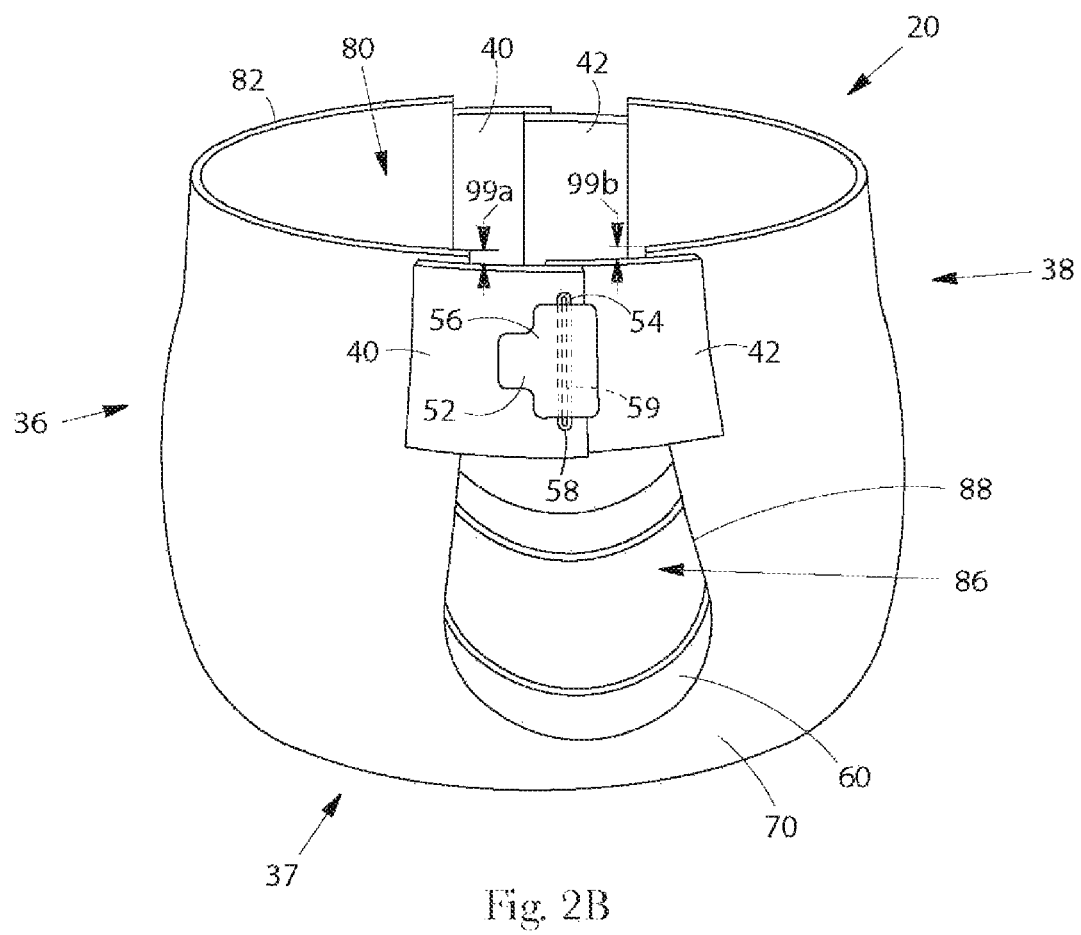
FIG. 2B is a perspective view of the diaper of FIG. 1B in a fastened configuration as would be exhibited during wear.

FIG. 1B depicts a diaper 20 having front and back ears 40, 42. The diaper may have a fastening system 50 comprising an engaging member 52 and a receiving member 54. The engaging member 52 may be disposed proximate the distal edge 43b of the back ear 42. The receiving member 54 may be disposed proximate the distal edge 41b of the front ear. In the FIG. 1B, the engaging member 52 is depicted as a tab member 56 and the receiving member 54 is depicted as a slot member 58 with a slot 59 therethrough. In a simple form, the fastening system 50 may be fastened by passing the tab member 56 completely through the slot 59 of the slot member 58. Once the tab member 56 has been passed through the slot member 58, the tab member 56 may be rotated into a plane generally parallel with the plane of the slot member 58 such that at least a part of the tab member 56 overlaps at least a portion of the slot member 58. FIG. 2B is a perspective view of the diaper 20 of FIG. 1B in a fastened configuration as would be seen during normal wear of the diaper 20. The tab member 56 and the slot member 58 are joined to form a leg opening 86 defined by a leg edge 88 (which includes a portion of the longitudinal edge 12, the lower edge 41*d* of the front ear 40, and the lower edge 43*d* of the back ear 42) and a waist opening 80 defined by a waist edge 82 (which includes a portion of the lateral edges 14 of the chassis 22, the upper edge 41*c* of the front ear, and the upper edge 43*c* of the back ear 42). In embodiments where the front ear 40 or the back ear 42 is extensible or elastic, the ear 40, 42 may be extended to provide a tensioning force to the diaper 20 during wear. It should be recognized that other suitable engaging member 52 and receiving member 54 combinations may be used instead or in addition to the tab and slot.

FIGS. 1A-C and 2A-B include a front tophat 99*a* and/or a back tophat 99*b*. In FIG. 1A, the back tophat 99*b* is shown in the rear waist region 38 as the portion of the diaper 20 bounded by the upper edge 43*c* of the back ear 42 and the lateral edge 14 in the rear waist region 38. Once fastened, as shown in FIG. 2A, the diaper 20 may have a front tophat 99*a* in the front waist region 36. The front tophat 99*a* is the portion of the diaper 20 bounded by the upper edge 41*c* of the back ear 42 and the lateral edge 14 in the front waist region 36.

In FIGS. 1B and 2B, the front tophat 99*a* is shown in the front waist region 36 as the portion of the diaper 20 bounded by the upper edge 41*c* of the front ear 40 and the lateral edge 14 in the front waist region 36. The back tophat 99*b* is shown in the rear waist region 38 as the portion of the diaper 20 bounded by the upper edge 43*c* of the back ear 42 and the lateral edge 14 in the rear waist region 38.

In FIG. 1C, the back tophat 99*b* is shown in the rear waist region 38 as the portion of the diaper 20 bounded by the upper edge 43*c* of the back ear 42 and the lateral edge 14 in the rear waist region 38.

Figure 3A:
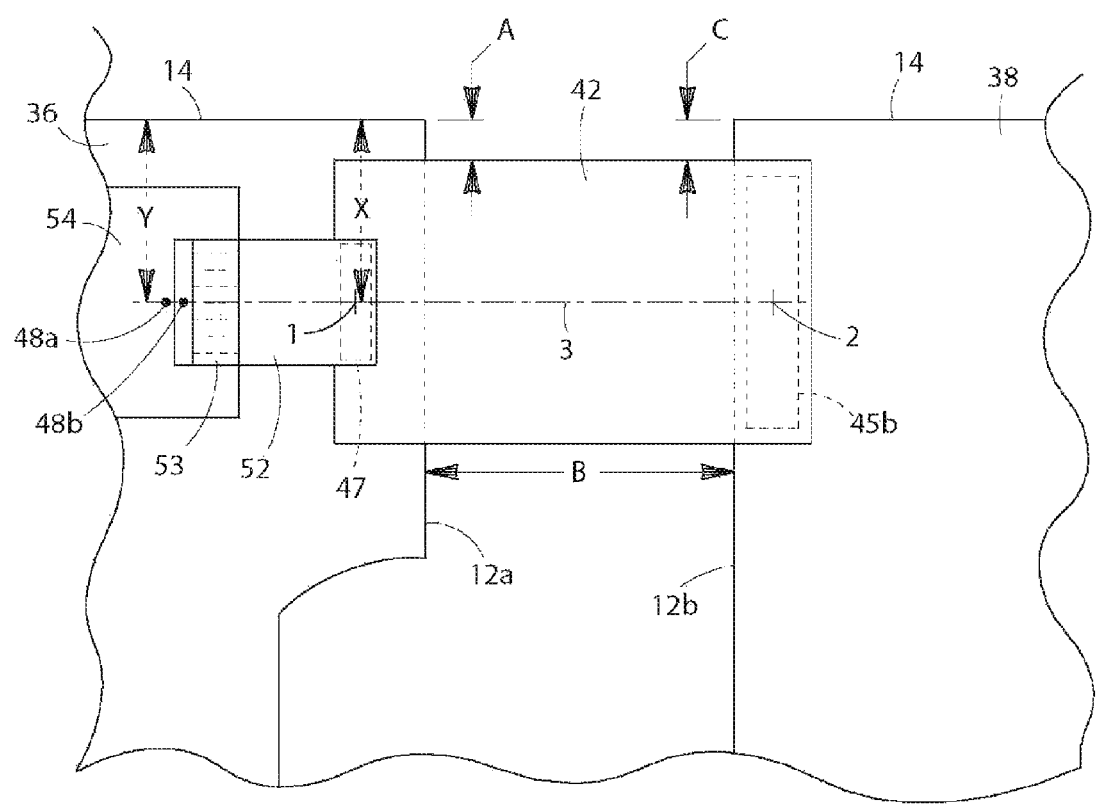
FIG. 3A is a magnified planar, side view of the diaper of FIG. 2A.
Figure 3B:
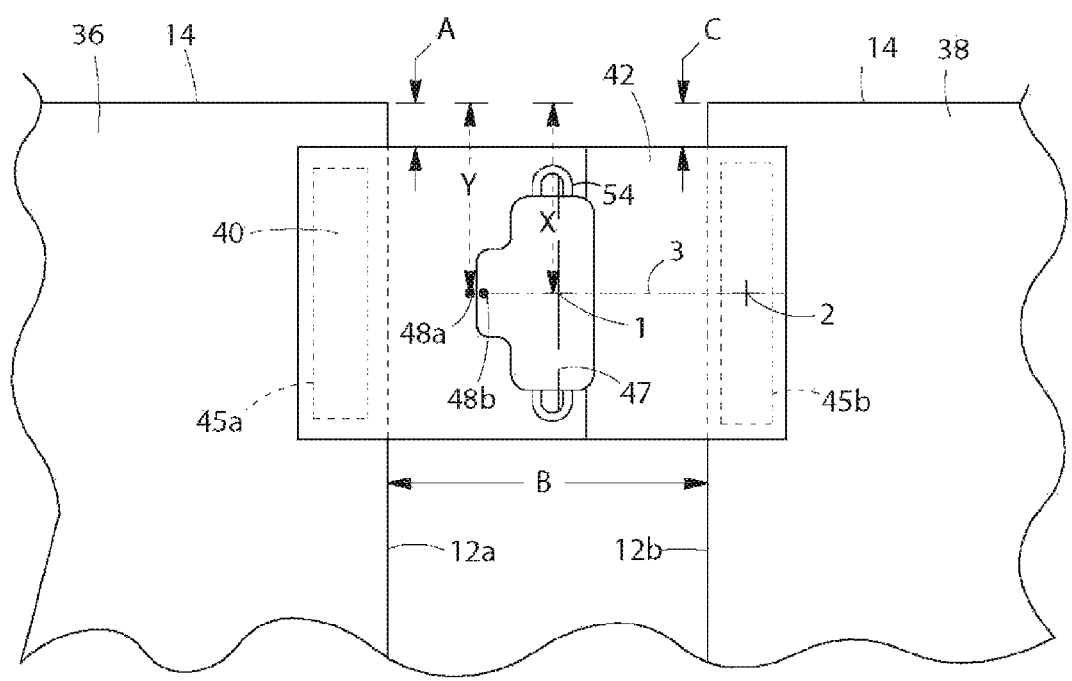
FIG. 3B is a magnified planar, side view of the diaper of FIG. 2B.

FIG. 3A is a magnified planar, side view of the diaper 20 of FIG. 2A showing the back ear 42, a portion of the front waist region 36, and a portion of the rear waist region 38. FIG. 3B is a magnified planar, side view of the diaper 20 of FIG. 2B showing the back ear 42, the front ear 40, a portion of the front waist region 36, and a portion of the rear waist region 38. To more precisely and quantitatively describe the tophats 99*a* and 99*b*, a number of metrics are shown. Suitable metrics include a Front Edge Displacement A, a Rear Edge Displacement C, an Ear Span Width B, an Ear Midpoint Width X, and a Receiving Member Midpoint Width Y. Several of the metrics are determined, with reference to a first product mark 1, a second product mark 2, and a lateral reference line 3. The receiving member 54 may include a longitudinal midpoint 48*a*. The engaging member may include a longitudinal midpoint 48*b*. The method for measuring the metrics and applying the product marks 1 and 2, the lateral reference line 3, the midpoints 48*a*, 48*b* to the diaper 20 is discussed below in the Metric Test Method section.

To address the problem of tophatting, it is desirable that the Front Edge Displacement A and the Rear Edge Displacement C be reduced or eliminated. In certain embodiments, the Front Edge Displacement A may be no greater than about 1.0 mm. Alternatively, the Front Edge Displacement A may be no greater than about 0.5 mm or about 0.3 mm. In certain embodiments, the Front Edge Displacement A may be about 0. In certain embodiments, the Rear Edge Displacement C may be no greater than about 10 mm. Alternatively, the Rear Edge Displacement C may be no greater than about 7 mm, about 5 mm, about 3 mm, or about 1 mm. In certain embodiments, the Rear Edge Displacement C may be about 0. Any combination of the aforementioned Front Edge Displacement A and Rear Edge Displacement C is also within the scope of the invention. Furthermore, in certain embodiments, the sum of the Front Edge Displacement A and the Rear Edge Displacement C may be no greater than about 12 mm. Alternatively, the sum of the Front Edge Displacement A and the Rear Edge Displacement C may be no greater than about 10 mm, about 5 mm, about 3 mm, or about 1 mm. In certain embodiments, the sum of the Front Edge Displacement A and the Rear Edge Displacement C may be about 0.

In other embodiments, it has been found that a ratio of the Front Edge Displacement A or Rear Edge Displacement C to the Ear Span Width B is very important in consumer perception of tophatting and the resulting waist edge discontinuity. For example, the waist edge discontinuity may be less appreciable in a diaper with a larger Ear Span Width B rather than with a diaper having a smaller Ear Span Width B. In certain embodiments, the ratio of the Front Edge Displacement A to the Ear Span Width B (A/B) may be no greater than about 0.05. In certain embodiments, the ratio of the Front Edge Displacement A to the Ear Span Width B (A/B) is about 0. In certain embodiments, the ratio of the Rear Edge Displacement C to the Ear Span Width B (C/B) may be no greater than about 0.24. Alternatively, the ratio of the Rear Edge Displacement C to the Ear Span Width B (C/B) may be no greater than about 0.20 or about 0.10. In certain embodiments, the ratio of the Rear Edge Displacement C to the Ear Span Width B (C/B) is about 0.

In other embodiments, it may be desirable that the combined Front Edge Displacement A and the Rear Edge Displacement C be minimized in relation to the Ear Span Width B. The sum of Front Edge Displacement A and the Rear Edge Displacement C to the Ear Span Width B ratio ((A+C)/B) may be no greater than about 0.30. Alternatively, the combined Front Edge Displacement A and the Rear Edge Displacement C to the Ear Span Width B ratio ((A+C)/B) may be less than about 0.20 or about 0.10. In other embodiments, the combined Front Edge Displacement A and the Rear Edge Displacement C to the Ear Span Width B ratio ((A+C)/B) is about 0.

In other embodiments, it has been found that a ratio of the Front Edge Displacement A to the Ear Midpoint Width X is very important in consumer perception of tophatting and the resulting waist edge discontinuity. For example, the waist edge discontinuity may be less appreciable in a diaper with a larger Ear Midpoint Width X rather than with a diaper having a smaller Ear Midpoint Width X. In certain embodiments, the ratio of the combined Front Edge Displacement A and the Rear Edge Displacement C to the Ear Midpoint Width X ((A+C)/X) may be less than about 0.30. Alternatively, the ratio of the combined Front Edge Displacement A and the Rear Edge Displacement C to the Ear Midpoint Width X ((A+C)/X) may be about 0.25, about 0.20, or about 0.10. In other embodiments, the ratio of the combined Front Edge Displacement A and the Rear Edge Displacement C to the Ear Midpoint Width X ((A+C)/X) is about 0.

FIGS. 1-3 depict the back ear 42 being bonded to and extending from the rear waist region 38 and designed such that the engaging member 52 joined to the back ear 42 may engage the receiving member 54 disposed in the front waist region 36. However, it should be readily apparent to one skilled in the art that the back ear may be configured to be a front ear 42 which may be bonded to and extend from the front waist region 36 and designed such that the engaging member 52 joined to the front ear may engage the receiving member 54 disposed in the rear waist region 38. The Front Edge Displacement A. Rear Edge Displacement C, Ear Span Width B, Ear Midpoint Width X, and the Receiving Member Midpoint Width Y are equally applicable to a front ear.

Metric Test Method

This method describes a method to mark and capture physical reference points on diapers as they are pulled to known tensile force values with a calibrated programmable mechanical tensile tester. This method also describes the process for making the appropriate distance calculations using spreadsheet software such as Microsoft Excel. These calculations are based upon measurements of pixel x-y coordinates taken from digital camera images through the use of photo-analysis computer program.

Figure 4:
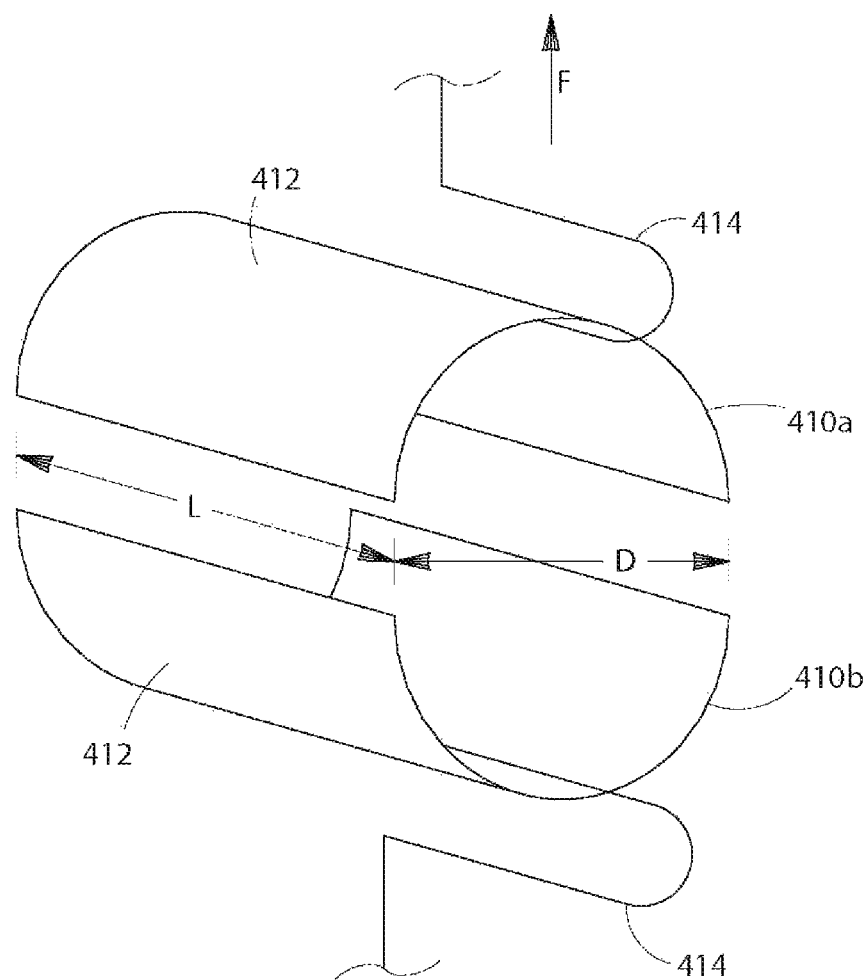
FIG. 4 is a perspective view of a suitable grip for use in the Metric Test Method.

A suitable tensile tester must be capable of pulling at a constant crosshead rate of 127 mm/min. The tensile tester must be equipped with a calibrated load cell such that the tested load values are no less than 1% of the calibration ranged of the load cell. A suitable tensile tester is a MTS Tensile Tester, Model 1/S available from MTS Systems Corp., Eden Prairie, Minn. and loaded with a 10N load cell. The tensile tester includes two matching grips 410a and 410b as shown in FIG. 4. Each grips 410a, 410b includes a semi-cylindrical face 412 upon which a sample may be mounted. The faces 412 are made from 1.50 mm thick stainless having a length L of 127 mm. The faces 412 have a diameter D of 115 mm. Each face 412 is joined to a hook 414 that allow the grip 410 to be joined to the tensile tested. The hook 414 runs the length L of the inside surface of the semi-cylindrical face. One grip 410a is joined to the load cell and movable crosshead of the tensile tester. The other grip 410b is joined to the non-moving base of the tensile tester.

All values reported below are an average of five random samples. To ensure the randomization of consumer commercial samples, the five samples are to be taken as follows:

(i) If the consumer commercial sample is sold individually (i.e., one sample may be individually purchased), then five consumer commercial samples are acquired.

(ii) If the consumer commercial sample is to be sold as a plurality (i.e., several samples are purchased as a single unit), then five pluralities are to be acquired. One sample from each of the five pluralities is randomly chosen for testing.

Product Marks:

Two product marks "+" are to be placed on the left side (i.e., the side of the product that would fall along the left side of a wearer during normal wear of the sample) of each sample prior to testing. The product marks may be made using a fine tip permanent marker or like device. The first product mark 1, as shown in FIGS. 3A-B, is made according to the following steps:

1. If the product has a fastener bonding zone 47 (as shown in FIG. 3A-B), the first product mark is placed in the center of the fastener bonding zone 47.
2. If the product has no fastener bonding zone 47, the first product mark is placed, in the center of the engaging surface 53.
3. If 1 or 2 are not available, the first product mark is placed in the center of the engaging member 52.

The second product mark 2, as shown in FIGS. 3A-B, is placed in the center of the back bond region 45b. A lateral reference line 3 is drawn through the first product mark 1 and the second product mark 2; the line 3 terminates at the inboard and outboard edge of the ear/engaging member combination.

Figure 5A:
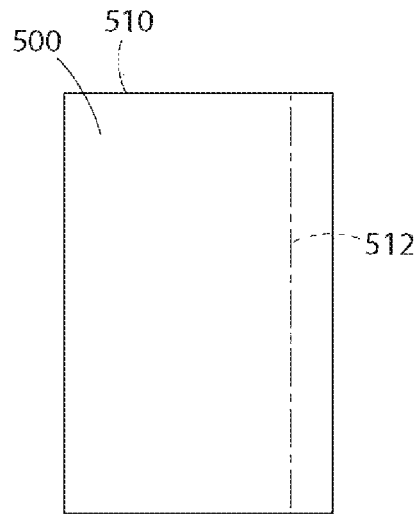
FIGS. 5A-C depict suitable edge determinations.
Figure 5B:
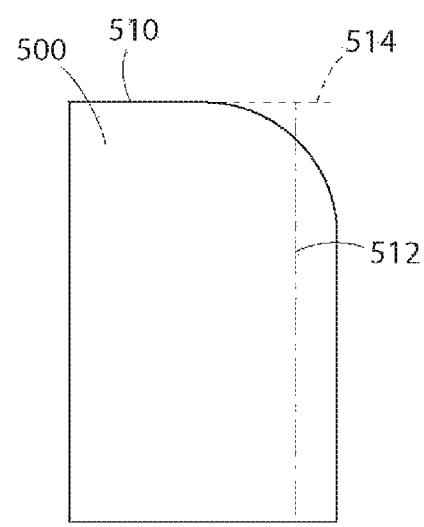

Metric Measurement:

The Front Edge Displacement A, Rear Edge Displacement C, Ear Span Width B, Ear Midpoint Width X, and the Receiving Member Midpoint Width Y may be determined, according to the description provided below and with reference to FIGS. 3A-B. For purposes of metric measurement and procedural steps, when measuring to or from an edge, the term "edge" means in order of preference:

1. A physical edge 510 of a sample 500 if said edge 510 is linear and intersects with a line segment 512 to be drawn, as shown in FIG. 5A,
2. If not 1, then a linear projection 514 from the physical edge 510 of the sample 500 if the physical edge 510 is substantially linear, as shown in FIG. 5B.
3. If not 1 or 2, then a tangential line 516 drawn from the outermost point 518 on the physical edge 510 of the sample 500, as shown in FIG. 5C.

Figure 5C:
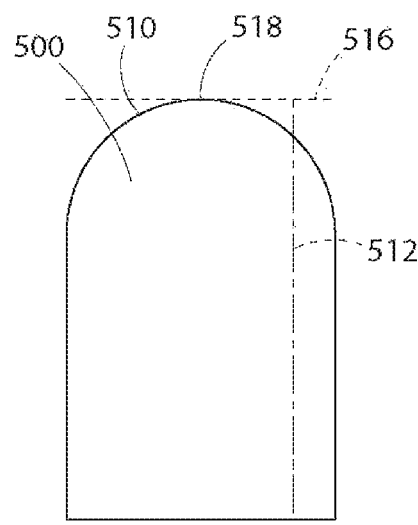

FIGS. 5A-C are provided to teach how the linear projection and tangential line should be drawn on a simple shape (e.g., sample 500). One skilled in the art will be able to apply these teachings to drawing the linear projection and tangential line on the various edges of an absorbent article.

The Front Edge Displacement A is the distance of a line segment drawn from (i) the intersection of the upper edge of the ear and the front longitudinal edge 12a and perpendicular to (ii) the lateral edge 14 in the front waist region 36, a linear projection of the lateral edge 14 in the front waist region 36, or, for samples where there is no linear component of the edge, a tangent line drawn from the edge. As shown in FIG. 3A, the Front Edge Displacement A is the distance between the upper edge 43c of the back ear 42 and the lateral edge 14 of the front waist region 38. As shown in FIG. 3B, the Front Edge Displacement A is the distance between the upper edge 41c of the front ear 40 and the lateral edge 14 of the front waist region 38.

The Rear Edge Displacement C is the distance of a line segment drawn from (i) the intersection of the upper edge of the ear and the rear longitudinal edge 12b and perpendicular to (ii) the lateral edge 14 in the rear waist region 38 or a linear projection of the lateral edge 14 in the rear waist region 38. As shown in FIGS. 3A and 3B, the Rear Edge Displacement C is the distance between the upper edge 44c of the back ear 42 and the longitudinal edge 14 of the rear waist region 38.

The Ear Span Width B is the linear distance of a line segment drawn from (i) the intersection of the lower edge of a back ear with either the front longitudinal edge 12a or an edge of the front ear 40, whichever is most outboard and (ii) the intersection of the rear longitudinal edge 12b and a lower edge of a back ear. As shown in FIG. 3A, the Ear Span Width B is the distance between (i) the intersection of the front longitudinal edge 12a and the lower edge 43d of the back ear 42 and (ii) the intersection of the rear longitudinal edge 12b and the lower edge 43d of the back ear 42. However, for side fastened diapers, such as shown in FIG. 3B, the Ear Span Width B is the distance of a line segment drawn from (i) the intersection of the front longitudinal edge 12a and the lower edge 41d of the front ear 40 and (ii) the intersection of the rear longitudinal edge 12b and the lower edge 43d of the back ear 42.

The Ear Midpoint Width X is the distance of the line segment drawn from (i) the first product mark 1 and perpendicular to (ii) the lateral edge 14 in the front waist region 36 or a linear projection of the lateral edge 14 in the front waist region 36.

The Receiving Member Midpoint Width Y is the distance of the line segment drawn from (i) a midpoint 48 of the receiving member 54 adjacent the inboard edge of the engaging member 52 (when the receiving member 54 and the engaging member 52 are in a fastened configuration) and perpendicular to (ii) the lateral edge 14 in the front waist region 36 or a linear projection of the lateral edge 14 in the front waist region 36. The longitudinal midpoint 48 of the receiving member 54 is the midpoint of a line segment drawn longitudinally from opposing lateral edges of the receiving member 54. In some instances such as shown in FIG. 3B, the receiving member 54 may be overlapped by the engaging member 52. In such instances, the midpoint 48 of the receiving member 54 is the midpoint of a line segment drawn longitudinally from the linear projection of the opposing lateral edges of the receiving member 54 and drawn adjacent to the inboard edge of the engaging member 52.

Procedural Steps:

The metrics are measured according to the steps that follow:

1. A calibration ruler is placed in proximity to the grips. The calibration ruler marked in millimeters is mounted so the ruled-face of the ruler is on the same plane as the surface of the product being measured.
2. A digital camera is mounted on a tripod adjacent to the tensile tester and positioned in such a way that the sample and calibration ruler fill the camera's field of view as much as possible. The camera is aligned vertically and horizontally with the surface of the sample.
3. The sample is marked with the two product marks and the lateral reference line as described above.
4. The sample is fastened to the sample's largest possible fastener setting. The engaging member should be joined to the receiving member such that a longitudinal midpoint of the engaging member is aligned longitudinally, at the point of intersection, with a longitudinal midpoint of the receiving member. The longitudinal midpoint of the receiving member is the midpoint of a line segment drawn longitudinally from opposing lateral edges of the receiving member. The longitudinal midpoint of the engaging member is the midpoint of a line segment drawn longitudinally from opposing lateral edges of the engaging member. Additionally, the proximal edge of the engaging surface should be aligned with the longitudinal edge of the receiving surface. In samples not having a distinct engaging surface or receiving surface, the engaging member and receiving member of the sample should be fastened such that (i) the lateral edges in the front and back waist regions are aligned and (ii) the distal edge of the engaging member is placed 50 mm inboard of the longitudinal edge of the front waist region or as far outboard as possible while still maintaining engagement to the front waist region, whichever results in the fastener being closer to the longitudinal edge of the front waist region.
5. The sample is mounted onto the grips of the tensile tester such that the front waist region of the sample is approximately centered on the movable grip and that the back waist region of the sample is approximately centered on the stationary grip. The sample is mounted sample so that the sample marks are facing the camera, all test values are visible, the sample is at the same distance from the camera as the ruler, and the sample is perpendicular to the camera's field or view.
6. The sample is pulled at a constant crosshead rate of 127 mm/min and held, in position for 10 seconds when the load reaches 200 grams. A picture is taken.
7. The sample is pulled at a constant crosshead rate of 127 mm/until a load value of 1200 grams is reached. The crosshead is stopped and a picture is taken.
8. The crosshead is returned, to the original position.

Using a computer imaging program capable of displaying pixel values in pictures (i.e., Adobe® Photoshop®), each picture taken at 1200 g load is analyzed. For each picture, a line is drawn on the digital image for each of the metrics (A, B, C, X, Y, and W). The pixel coordinates (x and y coordinates) for the end points of each drawn line are recorded. A line is drawn on the calibration ruler between two marks that are 50 mm apart. The pixel coordinates for this line are recorded. The pixel coordinates for endpoints of each metric and the calibration ruler are entered into an appropriate computer spreadsheet program (e.g., Microsoft® Excel®). The spreadsheet may be programmed to computer the distance between endpoints, as measured in pixels, according to the following equation:

$$d = \sqrt{(x_1^2 - x_2^2) + (y_1^2 - y_2^2)}$$

where d=distance between two points $(x_1, y_1)$ and $(x_2, y_2)$. The distance in pixels for the calibration ruler, which is known to be 50 mm, can be use to convert the distance in pixels of any of the metric measurements into a distance in millimeters. The spreadsheet is programmed to convert length values based on pixel coordinates in millimeters.

The procedural steps are performed for the five duplicate samples. The distance values for each metric are averaged and the average is recorded.

EXAMPLES

Example 1 is a suitable example of the present invention. The chassis of this present example is constructed according to the description provided, for a containment assembly in U.S. Pat. No. 5,151,092. The example has two back ears joined along the opposing rear longitudinal edges of the chassis. The back ears comprise a trilaminate with two outmost layers being a nonwoven available from BBA Nonwovens, Inc., Old Hickory, Tenn. as code HEC FPN 332D. Disposed between the two nonwoven layers is an elastic film available from Nordenia USA, Inc., Jackson, Mo. as code KG6361.100. A portion of the back ear is incrementally stretched, according to the zero strain activation processes disclosed in U.S. Pat. Nos. 5,167,897 and 5,156,793. The back ear further comprises an engaging member which is a polymer film tab with a hook-bearing surface. The hook-bearing surface has an approximate area of 3.8 cm². The tab extends from the outboard edge of the back ear opposite the back ear edge that is joined to the chassis. The example further comprises a rectilinear receiving member disposed in the front waist region and on the garment-facing surface of the chassis. The receiving member is a polymer film patch with fibrous loops on the garment-facing surface of the patch. The patch is available from Aplix Fasteners, Inc., Suffolk, UK as code AN29R95327873. The patch measures approximately 13.5 cm×5.0 cm with the long dimension running approximately parallel to the lateral edge of the chassis.

Example 2 is a commercially available comparative sample. The example is Pampers Cruisers size 4 diaper available from The Procter & Gamble Company, Cincinnati, Ohio.

Example 3 is a commercially available comparative sample. The example is Huggies® Supreme® size 4 available from the Kimberly-Clark Corp., Neenah, Wis.

Example 4 is a commercially available comparative sample. The example is Baby-Shaped® Huggies® size 4 available from the Kimberly-Clark Corp., Neenah, Wis.

Test Results

|  | A | B | C | A + C | X | Y |
|---|---|---|---|---|---|---|
| Example 1 | 0 (0) | 45.2 (5.7) | 5.7 (0.7) | 5.7 | 32.5 (1.5) | 33.8 (1.1) |
| Example 2 | 8.7 (2.8) | 64.1 (7.7) | 15.9 (1.4) | 24.6 | 47.1 (2.4) | 46.3 (1.7) |
| Example 3 | 5.2 (5.0) | 49.0 (3.2) | 17.8 (3.5) | 23.0 | 40.4 (4.9) | 43.8 (3.5) |
| Example 4 | 4.8 (2.6) | 29.2 (2.1) | 12.8 (2.5) | 17.6 | 44.1 (1.3) | 47.4 (1.6) |

All measurements in millimeters. Standard deviation presented in parenthesis.

|  | C/B | (A + C)/B | (A + C)/X |
|---|---|---|---|
| Example 1 | 0.13 | 0.13 | 0.18 |
| Example 2 | 0.25 | 0.38 | 0.52 |
| Example 3 | 0.36 | 0.47 | 0.57 |
| Example 4 | 0.44 | 0.60 | 0.40 |

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would, be obvious to those skilled in the art that various other changes and modifications can be made without departing from the spirit and scope of the invention. It should be apparent that combinations of such embodiments and features are possible and can result in executions within the scope of this invention. If is therefore intended, to cover in the appended claims all such changes and modifications that are within the scope of this invention.

What is claimed is:

1. A disposable absorbent article comprising:
   a) a chassis having a front waist region with a front waist edge, a rear waist region with a rear waist edge, a crotch region between the front waist region and the rear waist region, left and right longitudinal edges, and a longitudinal centerline dividing left and right sides of the chassis, the chassis comprising:
      i) a topsheet,
      ii) a backsheet, and
      iii) an absorbent core disposed between the topsheet and backsheet;
   b) left and right ears each having an upper lateral edge, a proximal edge, and a distal edge, wherein the left and right ears are joined respectively to the left and right sides of the chassis in the rear waist region such that at least a portion of each respective left or right ear extends laterally outward from the respective left or right longitudinal edge; and
   c) a fastening system comprising:
      i) an engaging member disposed proximate to the distal edge of each ear, the engaging member having disposed thereon a rectangular engaging surface with proximal and distal engaging surface edges parallel to the longitudinal centerline, the engaging surface having a center, and
      ii) a rectangular receiving member disposed on the chassis in the front waist region, the rectangular receiving member having left and right receiving member edges that are parallel to the longitudinal centerline, and top and bottom receiving member edges that are perpendicular to the longitudinal centerline, and a lateral axis through a longitudinal midpoint thereof, the receiving member being sized and positioned relative the front waist edge, and each of the left and right ears and engaging members being sized and positioned relative the rear waist edge, such that when the engaging surface on the engaging member of a left or right ear is placed with its center over the lateral axis of the receiving member proximate the respective left or right receiving member edge thereof,
   each ear has a Front Edge Displacement and a Rear Edge Displacement such that a sum of the Front Edge Displacement and the Rear Edge Displacement is no greater than about 12 mm.

2. The disposable absorbent article of claim 1 wherein the Front Edge Displacement for each ear is no greater than about 1 mm.

3. The disposable absorbent article of claim 1 wherein the Rear Edge Displacement for each ear is no greater than about 10 mm.

4. The disposable absorbent article of claim 1 wherein the article has an Ear Span Width for each ear; wherein a ratio of the sum of the Front Edge Displacement and the Rear Edge Displacement to the Ear Span Width for each ear is no greater than about 0.30.

5. The disposable absorbent article of claim 4 wherein the ratio of the sum of the Front Edge Displacement and the Rear Edge Displacement to the Ear Span Width for each ear is no greater than about 0.20.

6. The disposable absorbent article of claim 4 wherein a ratio of the Rear Edge Displacement to the Ear Span Width for each ear is no greater than about 0.20.

7. The disposable absorbent article of claim 6 wherein the ratio of the Rear Edge Displacement to the Ear Span Width for each ear is no greater than about 0.10.

8. The disposable absorbent article of claim 1 wherein each ear has an Ear Midpoint Width; wherein a ratio of the sum of the Front Edge Displacement and the Rear Edge Displacement to the Ear Midpoint Width for each ear is no greater than about 0.30.

9. The disposable absorbent article of claim 8 wherein the ratio of the sum of the Front Edge Displacement and the Rear Edge Displacement to the Ear Midpoint Width for each ear is no greater than about 0.20.

10. The disposable absorbent article of claim 1 wherein at least a portion of each ear is elasticized.

11. The disposable absorbent article of claim 1 wherein the fastening system is a hooks-to-loops system, hooks-to-hooks system, adhesive-to-polymeric film system; cohesive-to-cohesive system, adhesive-to-adhesive system; tab-to-slot system; or a button-to-button hole system.

12. The disposable absorbent article of claim 1 wherein the article is a prefastened disposable absorbent article.

* * * * *